United States Patent
Andino et al.

(10) Patent No.: US 6,907,294 B2
(45) Date of Patent: Jun. 14, 2005

(54) APPARATUS AND METHODS FOR FACILITATING WOUND HEALING

(75) Inventors: Rafael Andino, Lawrenceville, GA (US); Christopher Brooks, Glen Head, NY (US); Donald Van Royen, New York, NY (US)

(73) Assignee: Biofisica, LLC, Lawrenceville, GA (US)

( * ) Notice: Subject to any disclaimer, the term of this patent is extended or adjusted under 35 U.S.C. 154(b) by 19 days.

(21) Appl. No.: 10/620,727

(22) Filed: Jul. 15, 2003

(65) Prior Publication Data

US 2004/0015223 A1 Jan. 22, 2004

Related U.S. Application Data

(62) Division of application No. 09/872,956, filed on Jun. 1, 2001, now Pat. No. 6,631,294.

(51) Int. Cl.[7] .................................................. A61N 1/04
(52) U.S. Cl. ........................ 607/46; 607/149; 607/152
(58) Field of Search ........................... 607/2, 148, 149, 607/152, 153, 46, 48, 50; 604/20

(56) References Cited

U.S. PATENT DOCUMENTS

| | | | |
|---|---|---|---|
| 2,099,511 A | 11/1937 | Caesar | 188/408 |
| 3,918,459 A | 11/1975 | Horn | 128/419 R |
| 3,964,477 A | 6/1976 | Ellis et al. | 128/172.1 |
| 4,019,510 A | 4/1977 | Ellis | 128/172.1 |
| 4,142,521 A | 3/1979 | Konikoff | 128/82.1 |
| 4,233,965 A | 11/1980 | Fairbanks | 128/1.5 |
| 4,312,340 A | 1/1982 | Donadelli | 128/207.21 |

(Continued)

FOREIGN PATENT DOCUMENTS

| | | | |
|---|---|---|---|
| DE | 19503341 | * | 7/1995 |
| EP | 0027363 | * | 4/1981 |
| EP | 0 947 214 A2 | | 10/1999 |
| WO | 9206736 | * | 4/1992 |
| WO | WO 98/26838 | | 6/1998 |
| WO | WO 00/65993 | | 11/2000 |

OTHER PUBLICATIONS

Assimacopoulos, Dennis, "Low Intensity Negative Electric Current in the Treatment of Ulcers of the Leg Due to Chronic Venous Insufficiency," *American Journal of Surgery:* 115, 683–687 (1968).

Baker, Lucinda L., et al., "Effects of Electrical Stimulation on Wound Healing in Patients with Diabetic Ulcers," *Diabetes Care:* 20(3), 405–412 (1997).

(Continued)

*Primary Examiner*—Jeffrey R. Jastrzab
(74) *Attorney, Agent, or Firm*—Fish & Neave IP Group of Ropes & Gray LLC; James A. Leiz

(57) ABSTRACT

An electrode system is provided that generates a current flow that envelops and permeates an entire wound site. The electrode system includes two electrodes that are shaped and oriented to cause the current to flow from one electrode through the wound to the other electrode. A first electrode is applied to the wound site and the second electrode encircles the first electrode and is applied to the skin surrounding the wound cite. The two electrodes may be mounted to an oxygen-permeable layer that provides support for the electrodes and allows the wound site to breathe. An electrically insulative element may be disposed between the two electrodes. A power supply, which may be local to or remote from the electrode system, is provided for applying a voltage potential across the electrodes. In another suitable embodiment, the two electrodes are comprised of oppositely charged polymers.

13 Claims, 3 Drawing Sheets

U.S. PATENT DOCUMENTS

| | | | |
|---|---|---|---|
| 4,313,438 A | 2/1982 | Greatbatch | 128/207.21 |
| 4,314,554 A | 2/1982 | Greatbatch | 128/207.21 |
| 4,398,545 A | 8/1983 | Wilson | 128/798 |
| 4,509,535 A | 4/1985 | Bryan | 128/798 |
| 4,535,775 A | 8/1985 | Brighton et al. | 128/419 |
| 4,556,051 A | 12/1985 | Maurer | 128/1.5 |
| 4,619,252 A | 10/1986 | Ibbott | 128/82.1 |
| 4,846,178 A | 7/1989 | Fuxue et al. | 128/419 F |
| 4,846,181 A | 7/1989 | Miller | 128/421 |
| 4,895,153 A | 1/1990 | Takeuchi et al. | 128/421 |
| 4,895,154 A | 1/1990 | Bartelt et al. | 128/421 |
| 4,911,688 A | 3/1990 | Jones | 604/20 |
| 4,922,906 A | 5/1990 | Takeuchi et al. | 128/419 R |
| 4,982,742 A | 1/1991 | Claude | 128/798 |
| 4,989,607 A | 2/1991 | Keusch et al. | 128/640 |
| 5,395,398 A | 3/1995 | Rogozinski | 607/50 |
| 5,423,874 A | 6/1995 | D'Alerta | 607/72 |
| 5,433,735 A | 7/1995 | Zanakis et al. | 607/50 |
| 5,578,022 A | 11/1996 | Scherson et al. | 604/304 |
| 5,685,837 A * | 11/1997 | Horstmann | 604/20 |
| 5,814,094 A | 9/1998 | Becker et al. | 607/50 |
| 5,853,424 A | 12/1998 | Rise | 607/117 |
| 5,974,344 A | 10/1999 | Shoemaker, II | 607/50 |
| 6,122,550 A | 9/2000 | Kozhemiakin et al. | 607/101 |
| 6,181,963 B1 * | 1/2001 | Chin et al. | 604/20 |
| 6,411,853 B1 | 6/2002 | Millot et al. | 607/50 |
| 6,631,294 B2 * | 10/2003 | Andino et al. | 607/46 |

OTHER PUBLICATIONS

Biedebach, Mark C., "Accelerated Healing of Skin Ulcers by Electrical Stimulation and the Intracellular Physiological Mechanisms Involved," *Acupuncture and Electro–therapeutics Research:* 14(1), 43–60 (1989).

Carley, Patrick J., et al., "Electrotherapy for Acceleration of Wound Healing: Low Intensity Direct Current," *Arch. Phys. Med. Rehab.:* 66, 443–446 (1985).

Davis, Stephen C., et al., "Electrical Stimulation and Ultrasound in Wound Healing," *Dermatologic Clinics:* 11(4), 775–781 (1993).

Dayton, Paul D., et al., "Electrical Stimulation of Cutaneous Ulcerations A Literature Review," *Journal of the American Podiatric Medical Association:* 79(7), 318–321 (Jul. 1989).

Feedar, Jeffrey A., et al. "Chronic Dermal Ulcer Healing Enhanced with Monophasic Pulsed Electrical Stimulation," *Physical Therapy:* 71(9), 639–649 (1991).

Fleischli, John G., et al. "Electrical Stimulation in Wound Healing," *The Journal of Foot & Ankle Surgery:* 36(6), 457–461 (1997).

Gault, Walter R., et al. "Use of Low Intensity Direct Current in Management of Ischemic Skin Ulcers," *Physical Therapy:* 56(3), 265–269 (Mar. 1976).

Gentzkow, Gary D., et al., "Electrical Stimulation for Dermal Wound Healing," *Clinics in Podiatric Medicine and Surgery:* 8(4), 827–841 (1991).

Gentzkow, Gary D., et al., "Electrical Stimulation to Heal Dermal Wounds," *Journal of Dermatologic Surgery and Oncology:* 19(8), 753–758 (Aug. 1993).

Gilcreast, Darlene M., et al., "Effect of Electrical Stimulation on Foot Skin Perfusion in Persons with or at Risk for Diabetic Foot Ulcers," *Wound Repair and Regeneration:* 6(5), 434–441 (1998).

Gogia, Prem P., "Physical Therapy Modalities for Wound Management," *Ostomy/Wound Management:* 42(1), 46–54 (1996).

Itoh, Masayoshi, et al., "Accelerated Wound Healing of Pressure Ulcers by Pulsed High Peak Power Electromagnetic Energy (Diapulse)," *Decubitus:* 4(1), 24–34 (1991).

Kloth, Luther C., "Physical Modalities in Wound Management: UVC, Therapeutic Healing and Electrical Stimulation," *Ostomy/Wound Management:* 41(5), 18–27 (1995).

Kloth, Luther C., et al., "Promotion of Wound Healing with Electrical Stimulation," *Advances in Wound Care:* 9(5), 42–45 (Sept./Oct. 1996).

Kloth, Luther C., et al., "Acceleration of Wound Healing with High Voltage, Monophasic, Pulsed Current," *Physical Therapy:* 68(4), 503–508 (Apr. 1988).

Lee, Raphael C., et al., "A Review of the Biophysical for the Clinical Application of Electric Fields in Soft–Tissue Repair," *Journal of Burn Care and Rehabilitation:* 14(3), 319–335 (May/Jun. 1993).

Lundeberg, Thomas C.M., et al., "Electrical Nerve Stimulation Improves Healing of Diabetic Ulcers," *Annals of Plastic Surgery:* 29(4), 328–331 (1992).

Nicolle, Frederick V., et al., "Use of Radio–Frequency Pulsed Energy in the Control of Postoperative Reaction in Blepharoplasty," *Aesthetic Plastic Surgery:* 6, 169–171 (1982).

Rowley, Blair A., et al., "The Use of Low Level Electrical Current for Enhancement of Tissue Healing," *Biomedical Sciences Instrumentation:* 1, 111–114 (1974).

Šemrov, Dejáan et al., "DC Electrical Stimulation for Chronic Wound Healing Enhancement. Part 2. Parameter Determination by Numerical Modelling," *Bioelectrochemistry and Bioenergetics:* 43:271–277 (1997).

Stefanovska, A., et al., "Treatment of Chronic Wounds by means of Electric and Electromagnetic Fields—Part 2: Value of FES Parameters for Pressure Sore Treatment," *Medical & Biological Engineering Computing:* 31(3), 213–220 (May 1993).

Vodovnik, L., et al., "Treatment of Chronic Wounds by Means of Electric and Electromagnetic Fields—Part 1: Literature Review," *Medical & Biological Engineering & Computing:* 30(3), 257–266 (May 1992).

Weiss, Darryl S., et al., "Electrical Stimulation and Wound Healing," *Arch Dermatology:* 126, 222–225 (Feb. 1990).

Wheeler, Paul C., et al., "Neural Considerations in the Healing of Ulcerated Tissue by Clinical Electrotherapeutic Application of Weak Direct Current: Findings and Theory," *Neuroelectric Research:* 9, 83–99 (1971).

Wolcott, Lester E., "Accelerated Healing of Skin Ulcers by Electrotherapy: Preliminary Clinical Results," *Southern Medical Journal:* 62, 795–801 (Jul. 1969).

Yarkony, Gary M., "Pressure Ulcers: A Review," *Archives of Physical Medicine and Rehabilitation:* 75(8), 908–917 (1994).

* cited by examiner

APPARATUS AND METHODS FOR FACILITATING WOUND HEALING

This is a divisional of U.S. patent application Ser. No. 09/872,956, filed Jun. 1, 2001, now U.S. Pat. No. 6,631,294, which is hereby incorporated by reference herein in its entirety.

BACKGROUND OF THE INVENTION

The present invention relates generally to apparatus and methods for facilitating wound healing through the use of electrical stimulation, and more particularly to apparatus and methods for providing a voltage gradient and a pattern of current flow that envelopes and permeates the wound.

Connective tissue wound healing typically occurs in three distinct phases. Although these phases intertwine and overlap, each has a specific sequence of events that distinguishes it. During the initial, or inflammatory phase, the body begins to clean away bacteria and initiate hemostasis. The inflammatory phase has three subphases: hemostasis; leukocyte and macrophage migration; and epithelialization. This phase typically lasts for about four days.

The second phase, the proliferative phase, is characterized by a proliferation of fibroblasts, collagen synthesis, granulation, and wound contraction. The proliferative phase typically begins about 48 hours after the wound is inflicted and can extend anywhere from two hours up to a week. In this phase, the fibroblast cells begin the synthesis and deposition of the protein collagen, which will form the main structural matrix for the successful healing of the wound.

In the third phase, the remodeling phase, the collagen production slows. The collagen that is formed in this stage is more highly organized than the collagen formed in the proliferative phase. Eventually, the remodeled collagen increases the tensile strength in the wound and returns the wound to about 80% of the skin's original strength.

This is the general process that occurs in healthy human beings. Patients that suffer from conditions which limit the flow of blood to the wound site are unfortunately not able to exhibit the normal wound healing process as described. In some patients this process can be halted. Factors that can negatively affect this normal wound healing process include diabetes, impaired circulation, infection, malnutrition, medication, and reduced mobility. Other factors such as traumatic injuries and burns can also impair the natural wound healing process.

Poor circulation, for varying reasons, is the primary cause of chronic wounds such as venous stasis ulcers, diabetic ulcers, and decubitus foot ulcers. Venous stasis ulcers typically form just above the patient's ankles. The blood flow in this region of the legs in elderly or incapacitated patients can be very sluggish, leading to drying skin cells. These skin cells are thus oxygen starved and poisoned by their own waste products and begin to die. As they do so, they leave behind an open leg wound with an extremely poor chance of healing on its own. Diabetic foot ulcers form below the ankle, in regions of the foot that have very low levels of circulation.

Similarly, decubitus ulcers form when skin is subjected to constant compressive force without movement to allow for blood flow. The lack of blood flow leads to the same degenerative process as described above. Paraplegics and severely immobile elderly patients which lack the ability to toss and turn while in bed are the main candidates for this problem.

Traditional approaches to the care and management of these types of chronic non-healing wounds have included passive techniques that attempt to increase the rate of repair and decrease the rate of tissue destruction. Examples of these techniques include antibiotics, protective wound dressings, removal of mechanical stresses from the affected areas, and the use of various debridement techniques or agents to remove wound exudate and necrotic tissue.

For the most part, these treatment approaches are not very successful. The ulcers can take many months to heal and in some cases they may never heal or they may partially heal only to recur at some later time.

Active approaches have been employed to decrease the healing time and increase the healing rates of these ulcers. These approaches may include surgical treatment as well as alterations to the wound environment. These alterations may include the application of a skin substitute impregnated with specific growth factors or other agents, the use of hyperbaric oxygen treatments, or the use of electrical stimulation. It has also been shown experimentally (both in animal and clinical trials) that specific types of electrical stimulation will alter the wound environment in a positive way so that the normal wound healing process can occur or in some cases occur in an accelerated fashion.

Therapeutic Electrostimulation

The relationship between direct current electricity and cellular mitosis and cellular growth has become better understood during the latter half of the twentieth century. Weiss, in Weiss, Daryl S., et. al., Electrical Stimulation and Wound Healing, Arch Dermatology, 126:222 (February 1990), points out that living tissues naturally possess direct current electropotentials that regulate, at least in part, the wound healing process. Following tissue damage, a current of injury is generated that is thought to trigger biological repair. This current of injury has been extensively documented in scientific studies. It is believed that this current of injury is instrumental in ensuring that the necessary cells are drawn to the wound location at the appropriate times during the various stages of wound healing. Localized exposure to low levels of electrical current that mimic this naturally occurring current of injury has been shown to enhance the healing of soft tissue wounds in both human subjects and animals. It is thought that these externally applied fields enhance, augment, or take the place of the naturally occurring biological field in the wound environment, thus fostering the wound healing process.

Weiss continues to explain, in a summary of the scientific literature, that intractable ulcers have demonstrated accelerated healing and skin wounds have resurfaced faster and with better tensile properties following exposure to electrical currents. Dayton and Palladino, in Dayton, Paul D., and Palladino, Steven J., Electrical Stimulation of Cutaneous Ulcerations—A Literature Review, Journal of the American Podiatric Medical Association, 79(7):318 (July 1989), also state that the alteration of cellular activity with externally applied currents can positively or negatively influence the status of a healing tissue, thereby directing the healing process to a desired outcome.

Furthermore, research conducted by Rafael Andino during his graduate tenure at the University of Alabama at Birmingham, also demonstrated that the presence of electrical fields (in this case induced by the application of pulsating electromagnetic fields) dramatically accelerated the healing rates of wounds created in an animal model. This research found that the onset and duration of the first two phases of the wound healing process, the inflammatory and proliferative phases, had been markedly accelerated in the treated wounds while the volume of collagen which had been synthesized by the fibroblasts was also markedly increased in the treated wounds. This resulted in the wounds healing in a much shorter amount of time. Similar findings from other researchers can be found in other wound healing literature.

U.S. Pat. No. 5,433,735 to Zanakis et al. and U.S. Pat. No. 4,982,742 to Claude describe various electro-stimulation apparatus and techniques for facilitating the regeneration and repair of damaged tissue. However, each of these references suffers from the disadvantage that the pattern of current flow generated with these electrode devices does not pass through all portions of the wound and thus, certain portions of the wound site may not be exposed to the beneficial effects of electrostimulation.

U.S. Pat. No. 4,911,688 to Jones describes a wound cover that includes a chamber that encloses fluid around the wound. One electrode is located in the chamber and another electrode is placed away from the wound on the skin. By using conductive liquid within the chamber, a circuit is completed allowing current to flow from the electrode in the chamber, through the liquid, wound, and surrounding tissue and skin to the other electrode. The liquid is introduced into the chamber and replaced using two ports, one port is used to introduce the liquid while at the same time the other port is used to remove the gas (when the wound cover is originally applied to the wound) or fluid within the chamber. This wound cover, however, is complicated to use and involves a delicate process of adding and replacing the conductive liquid.

In view of the foregoing, it is an object of the present invention to provide improved apparatus and methods for easily providing a voltage gradient and a pattern of current flow that envelops and permeates the entire wound site.

SUMMARY OF THE INVENTION

This and other objects of the invention are accomplished in accordance with the principles of the present invention by providing an electrode system that includes-two electrodes that are adapted for connection to a power source sufficient to cause a current to flow between them. The electrodes are shaped and oriented to cause a pattern of current flow that envelops and permeates the entire wound site. Such shapes and orientations may include a circular first electrode located at and covering the wound site and a second electrode shaped as a ring fully encircling the first electrode. The second electrode may be located outside or partially within the wound site. Other suitable shapes of the electrodes may include electrodes that are ovally shaped, rectangularly shaped, triangularly shaped or any other suitable shape where one electrode encircles the other electrode. The shape of the electrode may conform to the shape of the wound.

The two electrodes of the electrode system may be mounted to an oxygen-permeable top layer that is impermeable to water and water vapor. The top layer may provide support for the electrodes and may allow the wound site to breathe.

The electrode system may also include an electrically insulative element that is disposed between the two electrodes. The insulative element may ensure that most if not all of the current flow between the electrodes passes through the damaged and healthy surrounding tissue.

The power supply for applying a voltage potential across the electrodes may be local to or remote from the electrode system. In one suitable arrangement, the power supply is attached to the top layer of the electrode system. The power supply can be configured to provide a constant or varying voltage, a constant or varying current, or any other suitable electrical output to the electrodes to facilitate wound healing. For example, the power supply may be configured to provide the desired current or voltage to the electrodes at different time intervals with the same electrode system in place. In one suitable embodiment, the power supply is a battery. In another suitable embodiment, the power supply is electronic circuitry that is configured to provide the desired current or voltage.

In another suitable embodiment of the invention, the two electrodes of the electrode system are comprised of oppositely charged polymers of sufficient voltage differential and charge capacity to cause a current to flow from the first electrode to the second electrode through the wound.

The electrode system can be designed and fabricated to be either disposable or reusable.

The electrode system according to the various embodiments described herein is capable of generating a voltage gradient and a pattern of current flow that envelops and permeates the entire wound site. Such a pattern of current flow maximizes the recruitment of the necessary cells to the wound location at the appropriate times during the various stages of wound healing.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION OF THE PREFERRED EMBODIMENTS

Figure 1:
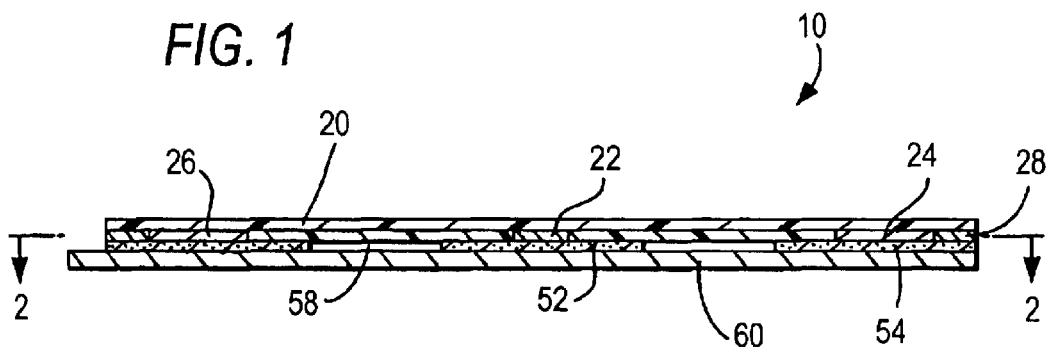
FIG. 1 is a cross-sectional view of an illustrative electrode system in accordance with the present invention taken generally along the line 1—1 of FIG. 2.
Figure 2:
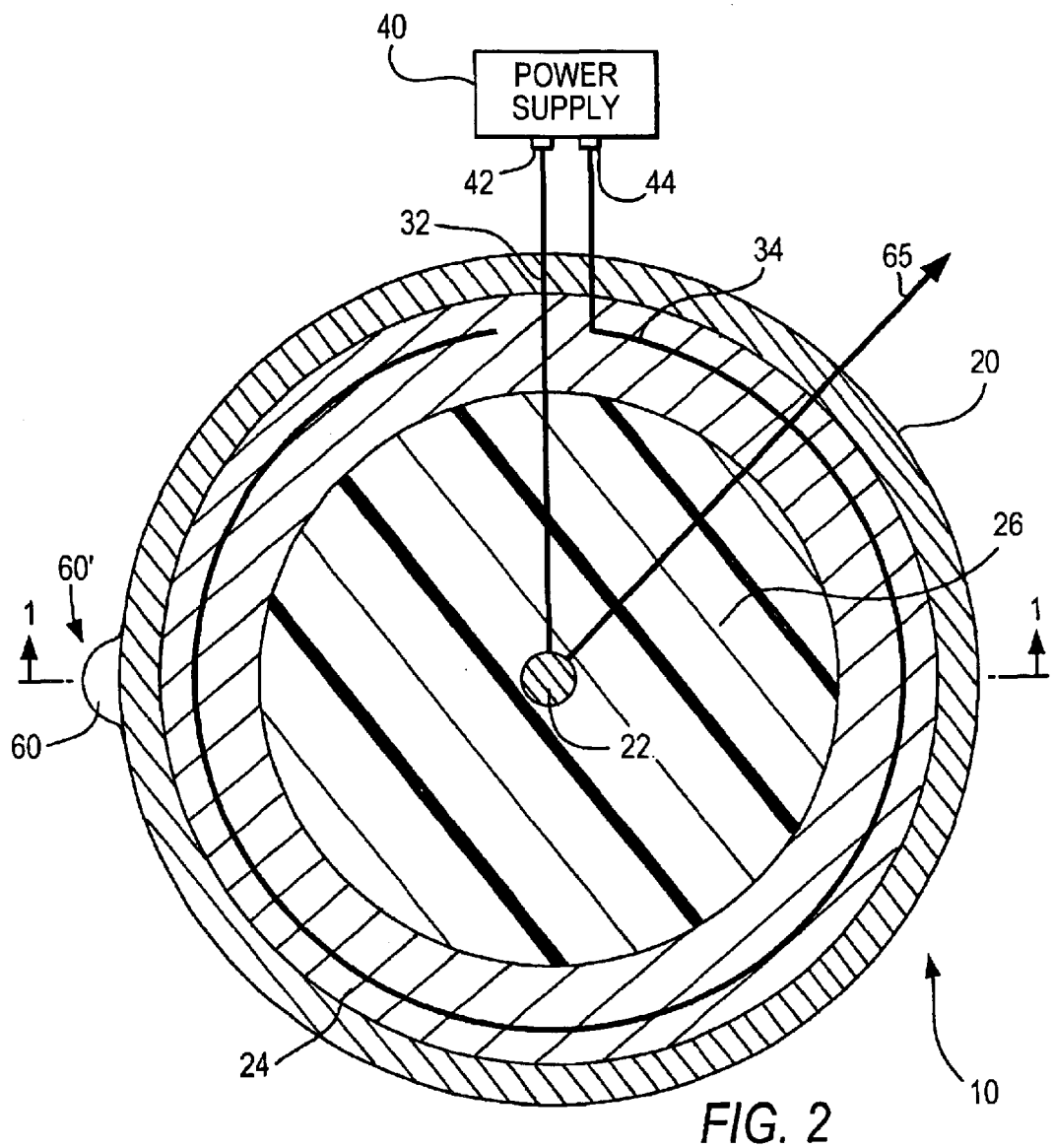
FIG. 2 is a cross-sectional view of the electrode system of FIG. 1 taken generally along the line 2—2 of FIG. 1

FIG. 1 is a cross-sectional view of electrode system 10. The view in FIG. 1 is taken along the line 1—1 of FIG. 2. FIG. 2 shows a simplified cross-sectional view of electrode system 10 taken alone the line 2—2 of FIG. 1. As illustrated in FIG. 1, electrode system 10 includes top overlay layer 20 to which electrodes 22 and 24, electrically insulative element 26, and end material 28 are attached. Electrode 22 is located towards the center of top overlay layer 20. Electrically insulative element 26 surrounds electrode 22 and electrode 24 surrounds electrically insulative element 26. Attached to the other side of electrodes 22 and 24, electrically insulative element 26, and end material 28 are adhesive layers 52 and 54. As illustrated in FIG. 2, electrically conductive lead 32 connects electrode 22 to terminal 42 of power supply 40 and electrically conductive lead 34 connects electrode 24 to terminal 44 of the power supply 40.

Top overlay layer 20 may serve several different purposes. First, top overlay layer 20 provides the mechanical integrity of electrode system 10, thus providing structural support for electrodes 22 and 24. Second, top overlay layer 20 should be flexible enough to allow electrode system 10 to conform to the contours of the skin surface to which it is adhered. Third, top overlay layer 20 should be oxygen permeable to allow the wound site to breathe. Finally, top overlay layer 20 should be water impermeable so that the wound site remains moist. In some embodiments, all of these characteristics may not be necessary. For example, a separate water impermeable layer may be used to keep the wound site moist. Top overlay layer 20 may be comprised of any suitable material or structure that exhibits these characteristics. For example, top overlay layer 20 may be comprised of a mesh structure of polypropylene, polyethylene, polyurethane, polytetrafluoroethylene (PTFE), or any other suitable material. In one embodiment, top overlay layer 20 can be electrically insulative to prevent current from flowing between electrodes 22 and 24, which are attached to top overlay layer 20. In another suitable embodiment, the adhesive or binding agent (not shown) used to adhere electrodes 22 and 24 to top overlay layer 20 can be electrically insulative to prevent current from flowing between electrodes 22 and 24.

Electrodes 22 and 24 may be thin metal, metallic paint or pigment deposition, metallic foil, conductive hydrogels, or any other suitable conductive material. Hydrogels are generally clear, viscous gels that protect the wound from dessicating. In one suitable approach, conductive hydrogels may be used as the material for electrodes 22 and 24 because of their permeability to oxygen and ability to retain water. Both oxygen and a humid environment is required for the cells in a wound to be viable. In addition, hydrogels can be easily cast into any shape and size. Various types of conductive hydrogels may be employed, including cellulose, gelatin, polyacrylamide, polymethacrylamide, poly(ethylene-co-vinyl acetate), poly(N-vinyl pyrrolidone), poly(vinyl alcohol), HEMA, HEEMA, HDEEMA, MEMA, MEEMA, MDEEMA, EGDMA, mathacrylic acid based materials, and siliconized hydrogels. PVA-based hydrogels are inexpensive and easy to form. The conductivity of such hydrogels can be changed by varying the salt concentration within the hydrogels. By increasing the salt concentration within a hydrogel, the conductivity of the hydrogel increases.

Insulative element 26 prevents the flow of current between electrodes 22 and 24 above the wound surface such as by moisture trapped under the top overlay layer. Insulative element 26 may be composed of any high resistance material such as polythylene, poly(tetrafluoroethylene) (TEFLON), polyurethane, polyester, a hydrogel made to be an insulator or any other suitable insulative material. In addition, insulative element 26 may be formed of a material or designed to have gaps or openings within its body to prevent the flow of current or greatly increase the current resistance above the wound surface.

End material 28 surrounds electrode 24. End material 28, in combination with the outer edge of top overlay layer 20, forms the outer edge of electrode system 10. End material 28 may be comprised of any suitable material flexible enough to allow electrode system 10 to conform to the contours of the skin surface to which it is adhered. In one embodiment, end material 28 may be composed of the same material as top overlay layer 20. In one suitable approach, end material 28 may be a part of and seamless with top overlay layer 20.

Conductive adhesive layers 52 and 54 are attached to the underside of electrode system 10, contacting electrodes 22 and 24, respectively and electrically insulative element 26. Adhesive layers 52 and 54 should be separated from each other by a suitable space or gap 58 to prevent short-circuiting of the electrodes. Adhesive layers 52 and 54 may be a hydrogel, fibrin, conductively transformed cyanoacrylates or can be comprised of any suitable electrically conductive material capable of attaching electrode system 10 to the skin and wound surfaces. Adhesive layer 52 can be arranged to distribute substantially the same voltage of electrode 22 to the entire surface of the wound. Similarly, adhesive layer 54 can be arranged to distribute substantially the same voltage of electrode 24 to the skin surrounding the wound. In another suitable approach, adhesive layer 52 can be arranged so that the center of adhesive layer 52 applies a voltage substantially similar to electrode 22 to the center of the wound and that the outer edge of adhesive layer 52 applies a voltage that is between the voltages of electrodes 52 and 54 to the outer edge of the wound. The voltage applied to the wound may be varied, for example, by varying the thickness of adhesive 52 or by any other suitable method.

As illustrated in FIG. 1, adhesive layer 52 extends beyond electrode 22. In another suitable arrangement, adhesive layer 52 may be the same size as or smaller than electrode 22. Adhesive layer 54 as illustrated is larger than electrode 24. In another suitable arrangement, adhesive layer 54 may be the same size as or smaller than electrode 24.

In another suitable embodiment, conductive adhesive layers 52 and 54 may be omitted from electrode system 10. In this embodiment, electrodes 22 and 24 are themselves adhesive and capable of attaching electrode system 10 to the wound site. Conductive hydrogels can be fashioned to have the requisite adhesive properties, thereby eliminating the need for separate adhesive layers. One type of highly conductive hydrogel that is sufficiently tacky and adhesive to adhere to the skin is described in U.S. Pat. No. 4,989,607 to Keusch et al. Electrodes 22 and 24 may be comprised of any suitable conductive adhesive material capable of attaching electrode system 10 to the wound site.

Backing layer 60 is attached to conductive adhesives 52 and 54 to protect the adhesive layer prior to the use of electrode system 10. Backing layer 60 may be peeled off of adhesives 52 and 54 to expose the adhesive layer prior to contacting electrode system 10 to the wound site. Backing layer 60 may protrude out from underneath top overlay layer 20 in one area, such as area 60' as shown in FIG. 2, to allow the user to easily remove backing layer 60 from electrode system 10.

In use, electrode system 10 is positioned over the wound site such that electrode 22 is located at approximate the center of the wound site and adhesive layer 52 can be sized to cover the entire wound. Electrode system 10 is provided in a family of sizes appropriate for wounds of various sizes. Electrode 24 and adhesive layer 54 are generally in the shape of a ring and are located a distance away from electrode 22. In one arrangement, the diameters of the inner edges of electrode 24 and adhesive layer 54 are greater than the diameter of the wound. In another words, the size of the wound determines the minimum inner diameter of electrode 24 and adhesive layer 54. In another suitable arrangement, adhesive layer 52 can be sized to cover the inner portion of the wound and the inner diameters of the inner edges of electrode 24 and adhesive layer 54 may be the same or less than the size of the wound.

Figure 3:
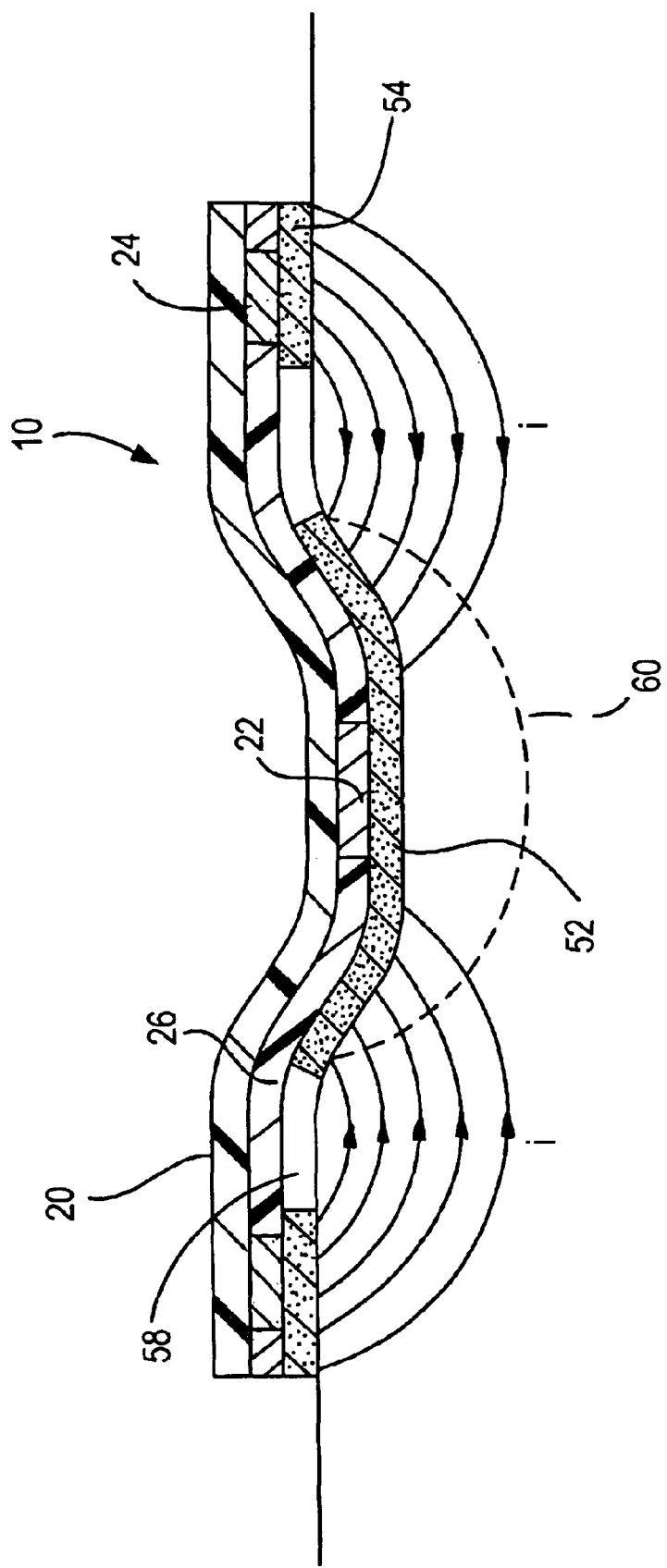
FIG. 3 is a cross-sectional view of the electrode system of FIG. 1 as applied to a wound that illustrates the pattern of current flow generated by the electrode system in accordance the present invention.

FIG. 3 is a cross-sectional view of electrode system 10 as applied to wound 60. As shown in FIG. 3, the pattern of current flow generated by electrode system 10 is toroidal in shape. A toroid is generally formed by rotating a circular disk about an axis, where the axis lies in the plane of the disk, but outside of the disk. Here, the pattern of current flow is similar to a semicircle rotated about an axis, where the axis lies in the plane of the semicircle and the axis is near the edge of the semicircle. The current generally flows tangential to the radial lines of the semicircle. Because electrode 24 surrounds electrode 22, the pattern of current flow is similar to the semicircular disk rotated completely around the axis. Therefore, the pattern of current flow is toroidal in shape. The pattern of current flow as illustrated in FIG. 3 would therefore generally be the same regardless of the angle of the cross-section cut through electrode system 10 with respect to reference direction 65 of FIG. 2. More specifically, as illustrated, electrode 22 is negatively charged and electrode 24 is positively charged. The lines of current flow extend from adhesive 54 through wound 60 to adhesive 52 in an arcuate shape. The lines of current pass through the entire wound 60, thereby enveloping and permeating the entire wound and the adjoining unwounded tissue. If the voltage that is applied to the wound from adhesive 52 is varied, as described above, then the current density at different portions of wound 60 can be increased or decreased accordingly. Electrode system 10 can produce a current density within the wound that is generally between 1 $\mu A/cm^2$ and 10,000 $\mu A/cm^2$. Depending on the size and nature of the wound, electrode system 10 may be configured to produce a current density within the wound that is less than of 1 $\mu A/cm^2$ or greater 10,000 $\mu A/cm^2$.

Referring to FIG. 2, conductive leads 32 and 34, which connect electrodes 22 and 24 respectively to power supply 40, may be comprised of metal, conductive ink or any other suitable conductive material. In one suitable arrangement, leads 32 and 34 are comprised of conductive carbon ink that is screened onto top overlay layer 20. In such an arrangement, electrodes 22 and 24 are formed in place over conductive leads 32 and 34, respectively.

Power supply 40 generates a voltage that is applied to electrodes 22 and 24 through leads 32 and 34, respectively. Power supply 40 may be configured to apply a voltage that is anywhere between 1 mV and 9 V. The resulting current flow that flows through the wound may be between 1 $\mu A$ and 50 mA. Depending on the size and nature of the wound, power supply 40 may be configured to apply a voltage that is less than 1 mV or greater than 9 V. The resulting current flow may therefore be less than 1 $\mu A$ or greater than 50 mA. Power supply 40 may be attached to the upper portion of top overlay layer 20 or any other suitable location on electrode system 10 or may be located remote from electrode system 10. In one suitable embodiment, power supply 40 is a battery. Power supply 40 may be any suitable battery such as an alkaline, nickel cadmium, or lithium battery. In one suitable arrangement, power supply 40 is a lithium polymer stack. The battery may be arranged so that terminal 42 is negative and terminal 44 is positive. Thus, electrode 22 functions as an anode and electrode 24 functions as a cathode. As described above, current will flow along outward radial lines from electrode 24 through the wound to electrode 22. In another suitable approach, the battery can be arranged so that terminal 42 is positive and terminal 44 in negative. In such an approach, the lines of current are reversed and directed outward from electrode 22 to electrode 24.

In another suitable embodiment, power supply 40 is comprised of electronic circuitry that is configured to provide a constant or varying voltage, a constant or varying current, or any other suitable electrical output. The current density within the wound site may therefore be constant or time varying. When power supply 40 varies the voltage or current, electrodes 22 and 24 may change polarities at a constant or at a time varying frequency. In another suitable electrical output, power supply 40 can be configured to pulse electrodes 22 and 24 to provide other possible therapeutic benefits.

In one suitable arrangement, the electrical circuitry can be configured to provide a constant current source using a current-to-voltage converter. The current to voltage converter may be probed at test points to check the current accuracy. The constant current source may be implemented with an operational amplifier (Op-amp). The Op-amp compares a precision voltage reference source to the output of a current-to-voltage converter and adjusts the output current until the reference and the converter are equal. The output voltage is limited to the battery voltage minus a certain predetermined amount used for operational purposes.

The circuit may be built with surface mount integrated circuits and other surface mount components and may be powered, for example, by lithium coin cell batteries.

The electrode system 10 herein described may not require a switch to be activated for current to commence flowing between electrodes 22 and 24. Rather, current may begin to flow following conductive contact of electrodes 22 and 24 to the wound site. Such contact completes a circuit between the electrodes and results in current flow between the electrodes. In another suitable embodiment, a switch may be located on electrode system 10 that may allow the user to engage and disengage power supply 40 to electrodes 22 and 24.

Electrode system 10 may contain within its circuitry a visual indicator to allow the user to determine whether or how well the electrode system is functioning. The visual indicator may be a light emitting diode (LED), a series of LEDs, a basic current meter, or any other suitable visual indicator.

Figure 4:
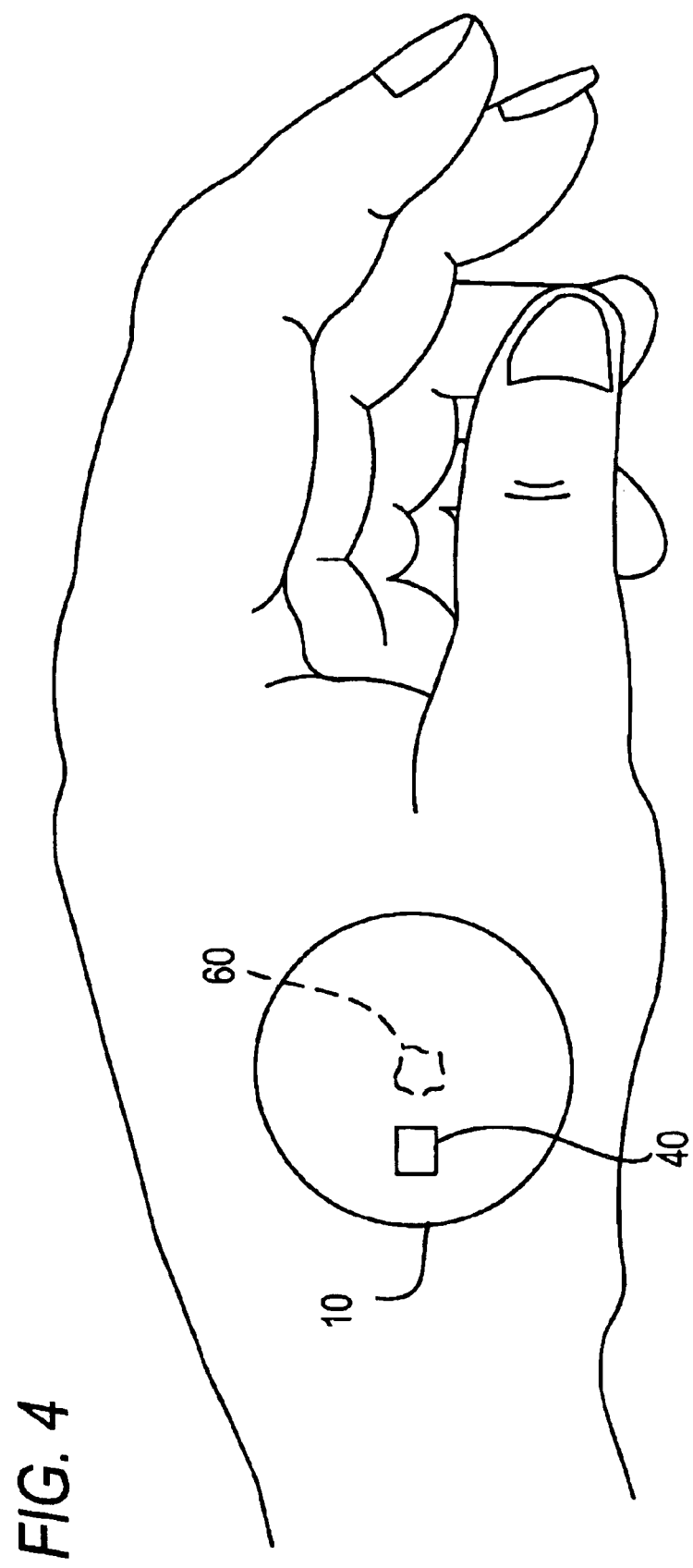
FIG. 4 is a perspective view of an illustrative electrode system placed over a wound site in accordance with the present invention.

FIG. 4 demonstrates a view of electrode system 10 placed over wound 60. In this embodiment, electrode system 10 is a disposable, one-time-use bandage that uses a battery and associated circuitry as power supply 40, which is attached to electrode system 10. Appropriate electrical parameters may be selected such that the current generated by the internal circuitry will last for a desired period of time. For example, the desired period of time may be at least as long as the typical amount of time a normal bandage is used on the wound. For users with chronic ulcers, this amount of time may typically be 1 to 2 days. Therefore, after electrode system 10 is activated by placement over the wound, an electrical current may last for 1 to 2 days. When it is time for electrode system 10 to be replaced, a new electrode system will be applied and the treatment will continue as required by the individual user and the type of wound present.

While electrode system 10 has been described as being generally circular in shape, it is understood that electrode system 10 may also be provided in other shapes as well. For example, electrode system 10 may be provided in an oval shape, rectangular shape, triangular shape, or any other suitable shape. The resulting pattern of current flow would therefore be similar to the toroidal shape described above which has been stretch from a circle to an oval shape, rectangular shape, triangular shape, or any other suitable shape of electrode system 10. Electrode system 10 is preferably provided in different shapes appropriate for wounds of different shapes. For example, if the wound is a long gash wound, a rectangular or oval shaped electrode system may be the appropriate shape for the wound. In one suitable approach, a preferred electrode system shape for a wound is a shape that will allow adhesive 52 to cover the entire wound and that will minimize the amount of area that adhesive 52 covers exterior to the wound. This will maximize the current flow through the wound.

In another suitable electrode system embodiment, electrodes 22 and 24 are electrically charged polymers. In this embodiment, power supply 40 and leads 32 and 34, as illustrated in FIGS. 1 and 2 are not required. In addition, top overlay layer 20 may not be required and electrodes 22 and 24 may be separately applied. Electrodes 22 and 24 can be oppositely charged polymers (e.g., hydrogel or any other suitable material for holding a charge) of sufficient differential voltage potential and of sufficient charge densities to cause a current to flow between the electrodes. In one suitable arrangement, electrode 22 is negatively charged and electrode 24 is positively charged. This would cause current to flow through the wound to negative electrode 22 from positive electrode 24. In another suitable arrangement, electrode 22 is positively charged and electrode 24 is negatively charged. This would cause current to flow from positive electrode 22 through the wound to negative electrode 24.

The foregoing is merely illustrative of the principles of this invention and various modifications can be made by those skilled in the art without departing from the scope and spirit of the invention.

What is claimed is:

1. An electrode system for facilitating the healing of a wound, comprising:
    a first electrode; and
    a second electrode, wherein the first and the second electrodes comprise oppositely charged polymers of sufficient differential-voltage potential and sufficient charge densities to cause a current to flow from the first electrode to the second electrode through the wound when the electrode system is applied to the wound.

2. The electrode system defined in claim 1 further comprising a support structure to which the first and second electrode are attached.

3. The electrode system defined in claim 2 wherein the support structure is permeable to oxygen.

4. The electrode system defined in claim 2 wherein the support structure is impermeable to water and water vapor.

5. The electrode system defined in claim 2 wherein the second electrode surrounds the first electrode on the support structure.

6. The electrode system defined in claim 5 further comprising an electrically insulative element attached to the support structure that is disposed between the first and the second electrodes.

7. The electrode system defined in claim 2 wherein the first electrode surrounds the second electrode on the support structure.

8. The electrode system defined in claim 7 further comprising an electrically insulative element attached to the support structure that is disposed between the first and the second electrodes.

9. The electrode system defined in claim 1 wherein the current that is caused to flow between the first and the second electrodes causes a current density within the range of 1 $\mu A/cm^2$ to 10,000 $\mu A/cm^2$ to occur through the area of the wound.

10. The electrode system defined in claim 1 further comprising:
    a first adhesive material attached to the first electrode, wherein the first adhesive material attaches the first electrode to the wound when the electrode system is applied to the wound; and
    a second adhesive material attached to the second electrode, wherein the second adhesive material attaches the second electrode to the skin surrounding the wound when the electrode system is applied to the wound.

11. The electrode system defined in claim 10 wherein the first electrode covers the entire wound when the electrode system is applied to the wound.

12. The electrode system defined in claim 1 further comprising:
    a first adhesive material attached to the first electrode, wherein the first adhesive material attaches the first electrode to the skin surrounding the wound when the electrode system is applied to the wound; and
    a second adhesive material attached to the second electrode, wherein the second adhesive material attaches the second electrode to the wound when the electrode system is applied to the wound.

13. The electrode system defined in claim 12 wherein the second electrode covers the entire wound when the electrode system is applied to the wound.

* * * * *

UNITED STATES PATENT AND TRADEMARK OFFICE
CERTIFICATE OF CORRECTION

PATENT NO. : 6,907,294 B2
DATED : June 14, 2005
INVENTOR(S) : Andino et al.

It is certified that error appears in the above-identified patent and that said Letters Patent is hereby corrected as shown below:

Title page,
Item [56], References Cited, OTHER PUBLICATIONS,
"Gentzkow" reference (second occurrence), delete "et al.";
"Kloth" reference (first occurrence), change "Healing" to -- Heating --;
"Semron" reference, change "Dejáan" to -- Deján --;
"Stefanouska" reference, insert -- & -- after "Engineering";

Column 3,
Line 40, change "includes-two" to -- includes two --;

Column 4,
Line 42, insert -- with -- after "dance";
Line 52, change "alone" to -- along --;

Column 5,
Line 47, change "polythylene" to -- polyethylene --;

Column 6,
Line 46, change "approximate" to -- approximately --;
Line 55, change "In another" to -- In other --;

Column 7,
Line 25, change "than of 1" to -- than 1 --.

Signed and Sealed this

Twenty-eighth Day of February, 2006

JON W. DUDAS
*Director of the United States Patent and Trademark Office*

UNITED STATES PATENT AND TRADEMARK OFFICE
CERTIFICATE OF CORRECTION

PATENT NO. : 6,907,294 B2  Page 1 of 1
APPLICATION NO. : 10/620727
DATED : June 14, 2005
INVENTOR(S) : Andino et al.

It is certified that error appears in the above-identified patent and that said Letters Patent is hereby corrected as shown below:

Col. 7, line 26, change "greater 10,000" to -- greater than 10,000 --;

Col. 7, line 57, change "44 in negative" to -- 44 is negative --;

Col. 8, line 58, change "stretch" to -- stretched --;

Col. 9, line 30, change "differential-voltage" to -- differential voltage --; and Col. 9, line 37, change "electrode" to -- electrodes --.

Signed and Sealed this

Seventeenth Day of June, 2008

JON W. DUDAS
*Director of the United States Patent and Trademark Office*